United States Patent
Cornish

(10) Patent No.: US 11,799,718 B2
(45) Date of Patent: Oct. 24, 2023

(54) SYSTEM FOR MANAGEMENT OF LAB MEASUREMENT DEVICES

(71) Applicant: Rohde & Schwarz GmbH & Co. KG, Munich (DE)

(72) Inventor: Matt Cornish, Fleet (GB)

(73) Assignee: Rohde & Schwarz GmbH & Co. KG, Munich (DE)

( * ) Notice: Subject to any disclaimer, the term of this patent is extended or adjusted under 35 U.S.C. 154(b) by 0 days.

(21) Appl. No.: 17/093,124

(22) Filed: Nov. 9, 2020

(65) Prior Publication Data

US 2022/0150115 A1     May 12, 2022

(51) Int. Cl.

| | |
|---|---|
| *H04L 41/0806* | (2022.01) |
| *G16H 40/40* | (2018.01) |
| *G16H 40/20* | (2018.01) |
| *G06F 16/955* | (2019.01) |
| *H04L 67/125* | (2022.01) |
| *G16H 10/40* | (2018.01) |
| *H04L 67/51* | (2022.01) |
| *G16H 40/67* | (2018.01) |

(52) U.S. Cl.
CPC ...... *H04L 41/0806* (2013.01); *G06F 16/9558* (2019.01); *G16H 10/40* (2018.01); *G16H 40/20* (2018.01); *G16H 40/40* (2018.01); *H04L 67/125* (2013.01); *H04L 67/51* (2022.05); *G16H 40/67* (2018.01)

(58) Field of Classification Search
None
See application file for complete search history.

(56) References Cited

U.S. PATENT DOCUMENTS

| | | | | |
|---|---|---|---|---|
| 6,477,569 | B1* | 11/2002 | Sayan | H04L 41/046 709/222 |
| 8,726,298 | B1* | 5/2014 | Desai | G10H 7/002 719/321 |
| 10,990,550 | B1* | 4/2021 | Juenger | G09G 5/006 |
| 2003/0035008 | A1* | 2/2003 | Fuller | G06F 9/451 715/771 |

(Continued)

OTHER PUBLICATIONS

Lee Teschler, Remote Communication with USBTMC, Jun. 21, 2019, https://www.testandmeasurementtips.com/remote-communication-with-usbtmc-faq/.*

(Continued)

*Primary Examiner* — Mohamed A. Wasel
*Assistant Examiner* — Gregory P Tolchinsky
(74) *Attorney, Agent, or Firm* — DITTHAVONG, STEINER & MLOTKOWSKI

(57) ABSTRACT

A system (1) for management of lab measurement devices is provided. The system (1) comprises a communication network (101), at least one bench (102), and a master PC (105). The at least one bench (102) comprises a bench PC (103) being connected to the communication network (101), and at least one measurement device (104) being connectable to the bench PC (103). The at least one measurement device (104) is associated with a device model (202). The master PC (105) is connected to the communication network (101), and is configured to manage the at least one measurement device (104), when connected to the bench PC (103), in accordance with its device model (202). In particular, the system (1) improves a manageability of training lab environments.

18 Claims, 6 Drawing Sheets

(56) References Cited

U.S. PATENT DOCUMENTS

| | | | | |
|---|---|---|---|---|
| 2005/0235292 | A1* | 10/2005 | Tillotson | G06F 9/4484 719/328 |
| 2008/0228908 | A1* | 9/2008 | Link | H04L 41/0853 709/223 |
| 2010/0281412 | A1* | 11/2010 | Cataldo | G06F 9/45512 715/771 |
| 2015/0208206 | A1* | 7/2015 | Heydlauf | H04W 4/33 455/411 |
| 2016/0091876 | A1* | 3/2016 | Keene | G08C 15/02 702/123 |
| 2016/0092175 | A1* | 3/2016 | Keene | G06F 9/46 717/113 |
| 2016/0253620 | A1* | 9/2016 | Pollock | G06Q 10/087 705/28 |
| 2019/0098093 | A1* | 3/2019 | Funahara | G01D 7/00 |
| 2019/0116087 | A1* | 4/2019 | Hiller | H04L 67/12 |

OTHER PUBLICATIONS

IEEE 488.2 Common Commands, WayBackMachine archived on Mar. 25, 2018, http://web.archive.org/web/20180325065240/https://na.support.keysight.com/pna/help/latest/Programming/GP-IB_Command_Finder/Common_Commands.htm.*

Configurations, WayBackMachine archived on Mar. 25, 2018, http://web.archive.org/web/20180325083728/http://na.support.keysight.com/pna/help/latest/Support/Configurations.htm.*

Keysight Technolgies, BenchVue Software, 2019, Published in USA, Jun. 1, 2019, 5991-3850EN, retrieved on Nov. 5, 2020 at https://www.keysight.com/us/en/assets/7018-04245/technical-overviews/5991-3850.pdf, 28 pages.

Tektronix, TekSmartLab, TBX3000A and TSL3000B, User Manual, 077-1110-02, retrieved on Nov. 5, 2020 at file:///C:/Users/SummerWu/Downloads/TekSmartLab-TBX3000A-TSL3000B-User-Manual-077111002-RevA.pdf, 146 pages.

* cited by examiner

SYSTEM FOR MANAGEMENT OF LAB MEASUREMENT DEVICES

TECHNICAL FIELD

The present invention relates to management of lab measurement devices, and in particular, to a system suited for such purpose.

BACKGROUND ART

Training courses on test and communication equipment typically involve a plurality of benches of measurement devices. The benches as well as their measurement devices assume particular communication means and require manual setup, configuration, maintenance and results collection. Commercially available lab management solutions suffer from proprietary hardware and/or software, restricted communication means, and ultimately fail to eliminate configuration and maintenance effort in large and/or varying training lab environments.

SUMMARY OF THE INVENTION

Accordingly, there is a need in the art to improve a manageability of training lab environments.

The invention is defined by the appended independent claims. Preferred embodiments are set forth in the dependent claims and in the following description and drawings.

According to a first aspect, a system for management of lab measurement devices is provided. The system comprises a communication network, at least one bench, and a master PC. The at least one bench comprises a bench PC being connected to the communication network, and at least one measurement device being connectable to the bench PC. The at least one measurement device is associated with a device model. The master PC is connected to the communication network, and is configured to manage the at least one measurement device, when connected to the bench PC, in accordance with its device model.

Preferably, the bench PC comprises a service application being configured to discover the at least one measurement device as it is connected to the bench PC, or as it is activated when connected to the bench PC; and report the device model of the discovered at least one measurement device to the master PC.

Preferably, the master PC comprises a service application being configured to discover the service application of the bench PC of the at least one bench; and receive the device model of the discovered at least one measurement device of the discovered bench PC.

Preferably, the service application of the master PC comprises a viewer being configured to graphically present the discovered at least one bench and the at least one measurement device of at least one bench, if any, using its device model; and provide a VNC and/or RDC link to the service application of the bench PC of the at least one bench.

Preferably, the service application of the master PC is configured to search for the at least one measurement device of the at least one bench given its device model.

Preferably, the at least one measurement device is connected to the bench PC via an Ethernet connection.

Preferably, the service application of the bench PC comprises a viewer being configured to provide a web link to the at least one measurement device being connected to the bench PC via the Ethernet connection.

Preferably, the service application of the bench PC comprises a DHCP server being configured to dynamically assign a network configuration parameter to the at least one measurement device as it is discovered by the bench PC via the Ethernet connection.

Preferably, the service application of the bench PC is configured to arrange for port forwarding to provide VXI-11 access to the at least one measurement device being connected to the bench PC via the Ethernet connection.

Preferably, the service application of the master PC is configured to discover the at least one measurement device of the at least one bench; and determine the device model of the discovered at least one measurement device.

Preferably, the at least one measurement device is connected to the bench PC via a USB TMC connection.

Preferably, the service application of the bench PC is configured to discover the at least one measurement device via the USB TMC connection based on USB connection event subscription.

Preferably, the service application of the bench PC comprises a VXI-11 server being configured to provide VXI-11 proxy access to the at least one measurement device being connected to the bench PC via the USB TMC connection.

Preferably, the service application of the bench PC is configured to register the VXI-11 server as a program with an ONC RPC port mapper.

Preferably, the VXI-11 server of the bench PC is configured to return, in response to a "*IDN?" SCPI command, a name of the at least one bench.

Preferably, the VXI-11 server of the bench PC is configured to return, in response to an "*OPT?" SCPI command, a pair of: the device model of the at least one measurement device, and a port for VXI-11 access to the at least one measurement device.

Preferably, the service application of the master PC is configured to save and/or recall data of the at least one measurement device of the at least one bench, the data being associated with the device model of the at least one measurement device.

Preferably, the data comprises SCPI commands, device configurations and/or measurement results.

Preferably, the service application of the master PC is configured to save data of a first one of the at least one measurement device of the at least one bench; and recall the saved data to a second one of the at least one measurement device of the at least one bench; the involved measurement devices being associated with the same device model.

Preferably, the service application of the master PC is configured to save data of the at least one measurement device of a first one of the at least one bench; and recall the saved data to the at least one measurement device of a second one of the at least one bench; the involved measurement devices being associated with the same device model.

BRIEF DESCRIPTION OF THE DRAWINGS

Further aspects, advantages and objects of the invention will become evident for the skilled reader by means of the following detailed description of the embodiments of the invention, when taking into conjunction with the figures of the enclosed drawings.

DETAILED DESCRIPTIONS OF EMBODIMENTS

The invention will now be described with respect to various embodiments. The features of these embodiments may be combined with each other unless specified otherwise.

Figure 1:
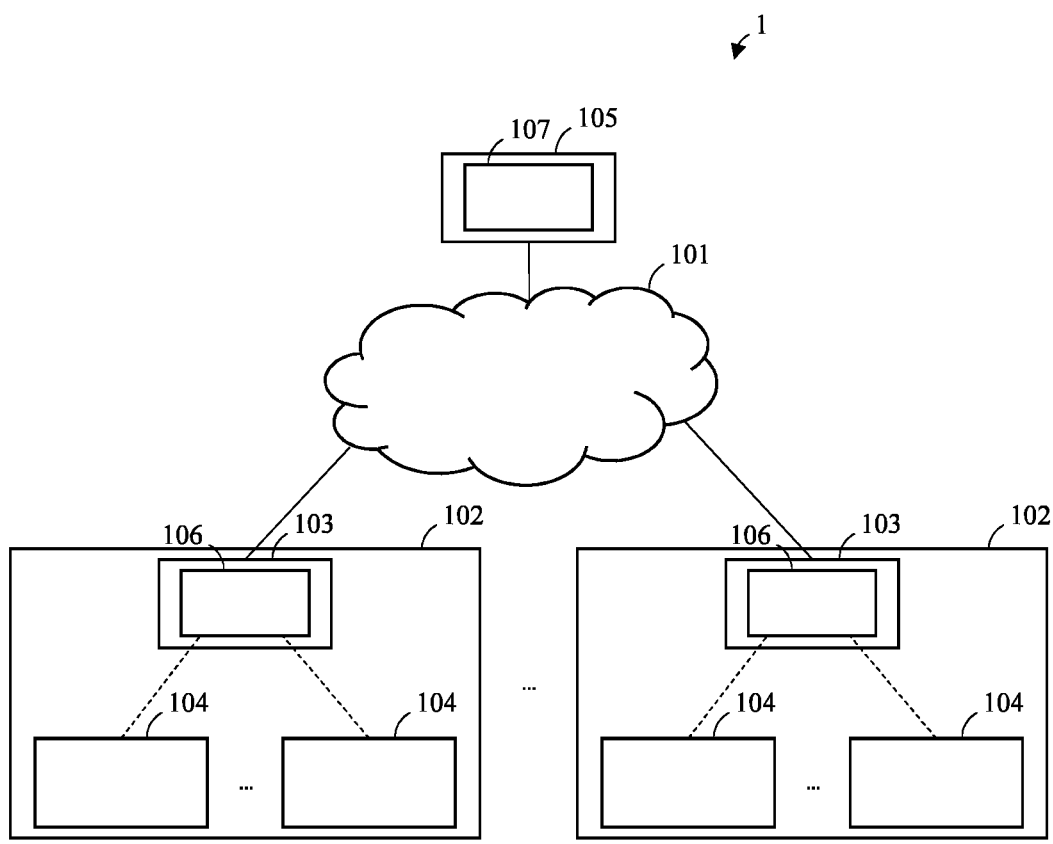
FIG. 1 illustrates a system for management of lab measurement devices according to an embodiment of the present disclosure.

FIG. 1 illustrates a system 1 for management of lab measurement devices 104 according to an embodiment of the present disclosure.

The system 1 comprises a communication network 101; at least one bench 102, and a master PC 105. As used herein, a bench may refer to a plurality of measurement devices forming a self-contained arrangement for at least one specific measurement purpose. The at least one bench 102, of which two exemplary bench instances are indicated in FIG. 1, comprises a respective bench PC 103 and at least one measurement device 104, of which two exemplary device instances are indicated per bench 102 in FIG. 1. The respective bench PC 103 may in particular be a general-purpose PC and is connected to the communication network 101. The at least one measurement device 104 is connectable to the respective bench PC 103, as is indicated by dashed lines, and associated with a device model 202 (not shown, see FIG. 2). In particular, the at least one measurement device 104 may be connected to the respective bench PC 103 via an Ethernet connection, or via a USB TMC connection, as will be explained in more detail in connection with FIGS. 4 and 6, in particular. The master PC 105 may in particular be a general-purpose PC and is connected to the communication network 101 and configured to manage the at least one measurement device 104, when connected to the respective bench PC 103, in accordance with the device model 202 of the at least one measurement device 104. Using off-the-shelf hardware improves a vendor independence of the system 1. In addition, using customer's existing PC hardware saves cost.

The respective bench PC 103 of FIG. 1 comprises a service application 106 being configured to discover the at least one measurement device 104 as it is connected to the respective bench PC 103, or as it is activated when already connected to the respective bench PC 103. The service application 106 is further configured to report the device model 202 of the discovered at least one measurement device 104 to the master PC 105. Accordingly, the service application 106 imparts control of each of the at least one measurement devices 104 of the particular bench 102. Consolidating control of the measurement devices 104 of a bench 102 in the service application 106 improves a manageability of the particular bench 102. In addition, auto-detection enables fully automatic delineation of a lab of many instruments into benches of instruments. This isolates measurement devices 104 of different benches 102. The service application 106 of the bench PC 103 is non-invasive in that it merely identifies and then detaches from measurement devices 104 at the time they are plugged in to the bench PC 103, it being a user action to plug-in a measurement device 104.

The master PC 105 of FIG. 1 comprises a service application 107 being configured to discover the service application 106 of the respective bench PC 103 of the at least one bench 102. The service application 107 is further configured to receive the device model 202 of the discovered at least one measurement device 104 of the discovered bench PC 103. Accordingly, the service application 107 imparts remote control of each of the at least one measurement devices 104 of the at least one bench 102. Consolidating control of the measurement devices 104 of all the benches 102 of the system 1 in the service application 107 improves a manageability of the whole system 1. In particular, the service application 107 of the master PC 105 is non-invasive in that does not control any measurement devices 104 to discover, organize or verify saved lab layouts (such as warning of missing instruments). Only explicit selection of a bench 102 will exert control and then only to specific measurement devices 104.

Figure 2:
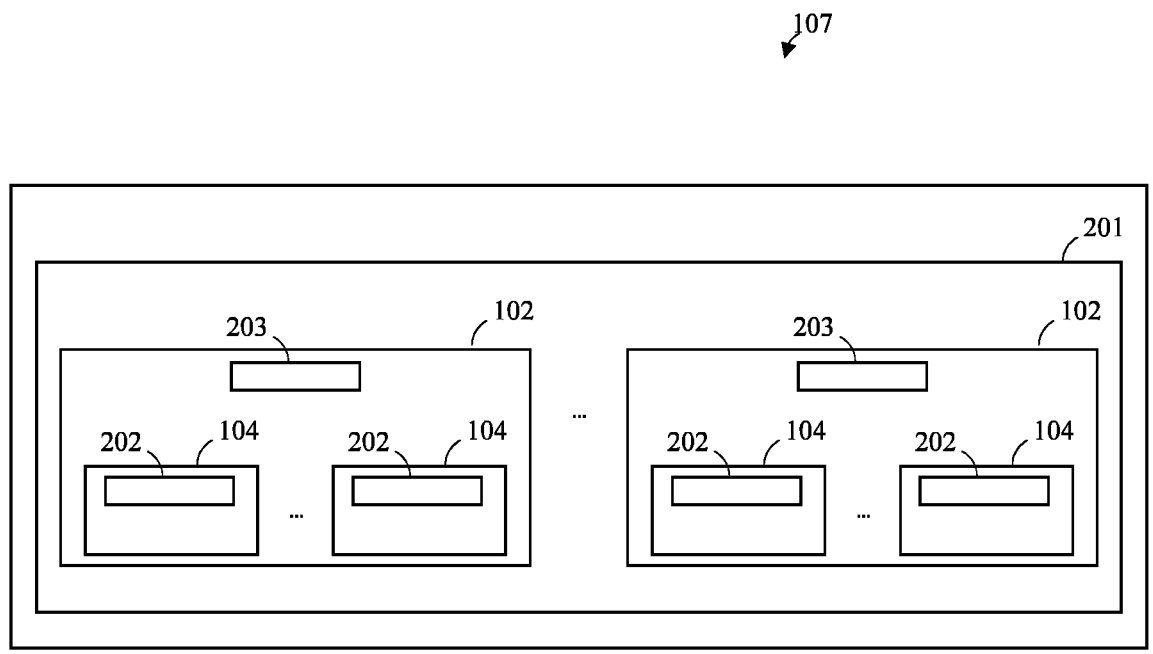
FIG. 2 illustrates a service application of the master PC of the system of FIG. 1.

FIG. 2 illustrates a service application 107 of the master PC 105 of the system 1 of FIG. 1.

The service application 107 of FIG. 2 comprises a viewer 201. The viewer 201 is configured to graphically present the discovered at least one bench 102, of which two exemplary bench instances are indicated in FIG. 2, and the at least one measurement device 104 of the at least one bench 102, of which two exemplary device instances are indicated per bench 102 in FIG. 2, using the device model 202 of the respective measurement device 104. In particular, this means that the at least one measurement device 104 is rendered with its associated device model 202 indicated. As such, the service application 107 imparts visibility of each of the at least one measurement devices 104 of the at least one bench 102 to a user. Consolidating visibility of the benches 102 of the system 1 in the service application 107 improves a manageability of the whole system 1.

The viewer 201 is further configured to provide a VNC and/or RDC link 203 to the service application 106 of the respective bench PC 103 of the at least one bench 102. As used herein, Virtual Network Computing (VNC) may refer to a graphical remote desktop-sharing system using the Remote Frame Buffer protocol (RFB) and a client-server approach in which a VNC client may remotely control another computer running a VNC server over a network connection. As used herein, a Remote Desktop Connection (RDC) may refer to a graphical remote desktop-sharing system using the proprietary Remote Desktop Protocol (RDP) protocol and a client-server approach in which an RDP client may remotely control another computer running an RDP server over a network connection. FIG. 2 shows one such link 203 per bench 102. Accordingly, the service application 107 imparts remote accessibility of each of the at least one measurement devices 104 of the at least one bench 102 to the user. Consolidating remote accessibility of the measurement devices 104 of all the benches 102 of the system 1 in the service application 107 improves a manageability of the whole system 1.

In addition, the service application 107 of FIG. 2 of the master PC 105 is configured to search for the at least one measurement device 104 of the at least one bench 102 given its device model 202, or other particulars of the sought-after measurement device 104. This further improves a manageability of the system 1.

Figure 3:
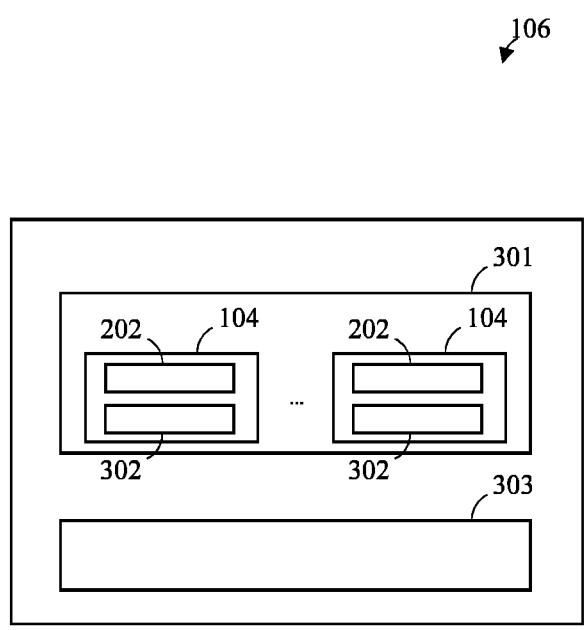
FIG. 3 illustrates a service application of a bench PC of the system of FIG. 1.

FIG. 3 illustrates a service application 106 of a bench PC 103 of the system 1 of FIG. 1.

The service application 106 of FIG. 3 comprises a viewer 301. The viewer 301 is configured to graphically present the at least one measurement device 104 of the respective one of the at least one bench 102, using the device model 202 of the respective measurement device 104. The viewer 301 is further configured to provide a web link 302 to the at least one measurement device 104 being connected to the bench PC 103. As such, the service application 106 imparts visibility and remote accessibility of each of the at least one measurement devices 104 of the at least one bench 102 to the user. Consolidating visibility and remote accessibility of the measurement devices 104 of a bench 102 in the service application 106 improves a manageability of the particular bench 102.

In particular, the at least one measurement device 104 may be connected to the bench PC 103 via an Ethernet connection. Such a LAN-based instrument connection supports Internet-based protocols. Preferably, in such case the service application 106 of the bench PC 103 comprises a DHCP server 303 being configured to dynamically assign a network configuration parameter, such as an IP address and/or further configuration parameters, to the at least one measurement device 104 as it is discovered by the bench PC 103 via the Ethernet connection. Such an auto-detection enables a fully automatic delineation of a lab of many instruments into benches of instruments. As used herein, the Dynamic Host Configuration Protocol (DHCP) may refer to a network configuration system in Internet Protocol (IP) based networks using a client-server approach in which a DHCP client may dynamically request network configuration parameters, including an IP address, from a DHCP server over a network connection. The DHCP server 303 may alternatively be hosted by any other device of the system 1, such as the master PC, for example. The DHCP server 303 simplifies and automates (re)configuration when changing a configuration of the particular bench 102. For example, substitution of a particular measurement device 104 by a spare measurement device merely requires (un)plugging the involved measurement devices in order to trigger auto-configuration of the IP address of the spare measurement device 104.

Figure 4:
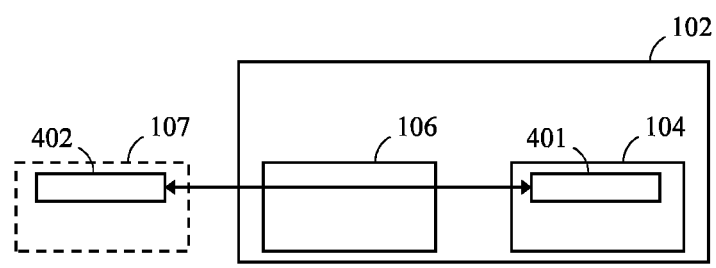
FIG. 4 illustrates remote VXI-11 access to the at least one measurement device when connected to its bench PC via an Ethernet connection.

FIG. 4 illustrates remote VXI-11 access to the at least one measurement device 104 when connected to its bench PC 103 via an Ethernet connection.

In FIG. 4, the at least one measurement device 104 is shown as being connected to the service application 106 of the bench PC 103 via the Ethernet connection. In this embodiment, the at least one measurement device 104 of the depicted at least one bench 102 comprises a VXI-11 server 401 being configured to provide VXI-11 access to the at least one measurement device 104 for a corresponding VXI-11 client 402, which may be operated remotely from the at least one bench 102. As used herein, the VMEbus Extensions for Instrumentation (VXI-11) may refer to a remote control system using an ASCII-based network instrument protocol and an Open Network Computing Remote Procedure Call (ONC RPC) model in which a VXI-11 client may call procedures in a VXI-11 server over a network connection, which in turn may provide access to its RPC services via a port mapper that listens for queries on one or more well-known ports. For example, FIG. 4 indicates by dashed lines that the service application 107 of the master PC 105 may comprise the VXI-11 client 402. Preferably, the service application 106 of the bench PC 103 is configured to arrange for port forwarding to provide VXI-11 access to the at least one measurement device 104, which is connected to the bench PC 103 via the Ethernet connection suggested by the arrow between the VXI-11 server 401 and the corresponding VXI-11 client 402. In such case, the service application 107 of the master PC 105 is configured to discover the at least one measurement device 104 of the at least one bench 102; and to determine the device model 202 of the discovered at least one measurement device 104 without any further assistance.

As a result, vendor-agnostic remote access to the at least one measurement device 104 is achieved based on Ethernet connectivity of the at least one measurement device 104. However, exposing measurement devices 104 to remote control via VXI-11 ports allows for swapping of instruments, regardless of the underlying USB/LAN connectivity. In particular, measurement devices 104 may be swapped/substituted without affecting saved layouts or saved settings.

Figure 5:
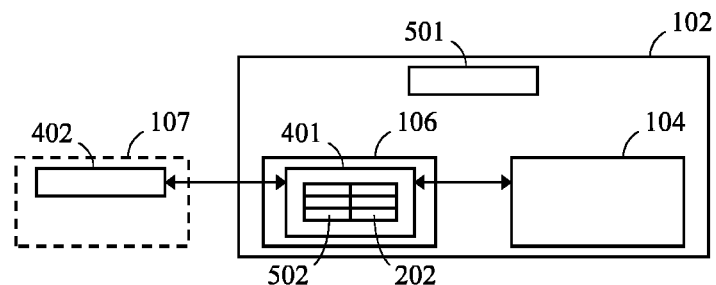
FIG. 5 illustrates remote VXI-11 access to the at least one measurement device when connected to its bench PC via a USB TMC connection.

FIG. 5 illustrates remote VXI-11 access to the at least one measurement device 104 when connected to its bench PC 103 via a USB TMC connection.

In FIG. 5, the at least one measurement device 104 is shown as being connected to the service application 106 of the bench PC 103 via the USB TMC connection. As used herein, the USB Test & Measurement Class (USB TMC) may refer to a remote control system using an extension of the Universal Serial Bus (USB) protocol and a Virtual Instrument Software Architecture (VISA) to remotely control test and measurement devices over a USB network connection. Utilizing USB instrument connection minimizes bench network hardware. In addition, measurement devices 104 may be disconnected from USB and reconnected via Ethernet (or vice-versa, e.g. to access a web page) without affecting saved layouts or settings. The service application 106 of the bench PC 103 is configured to discover the at least one measurement device 104 via the USB TMC connection based on USB connection event subscription. Such an auto-detection enables delineation of a lab of many instruments into benches of instruments, and simplifies a (re) configuration of the system 1 and further improves its manageability. In this embodiment, it is the service application 106 of the bench PC 103 that comprises the VXI-11 server 401 which is configured to provide VXI-11 proxy access to the at least one measurement device 104 for the corresponding VXI-11 client 402, which may be operated remotely from the at least one bench 102. Preferably, the service application 106 of the bench PC 103 is configured to register the VXI-11 server 401 as a program with an ONC RPC port mapper. In particular, the VXI-11 server of the bench PC 103 may be configured to return, in response to a "*IDN?" SCPI command, a name 501 of the at least one bench 102. As used herein, the Standard Commands for Programmable Instruments (SCPI) may refer to a command language for controlling measurement devices. The VXI-11 server 401 of the bench PC 103 may further be configured to return, in response to an "*OPT?" SCPI command, a pair of: the device model 202 of the at least one measurement device 104, and a port 502 for VXI-11 access to the corresponding measurement device 104. The service application 106 may thus act as a proxy between one or more VXI-11 clients 402 and one or more VXI-11 servers 401, which are associated with respective ports. As a result, vendor-agnostic remote access to the at least one measurement device 104 is achieved based on USB TMC connectivity of the at least one measurement device 104. However, exposing measurement devices 104 to remote control via VXI-11 ports allows for swapping of instruments, regardless of the underlying USB/LAN connectivity.

Figure 6:
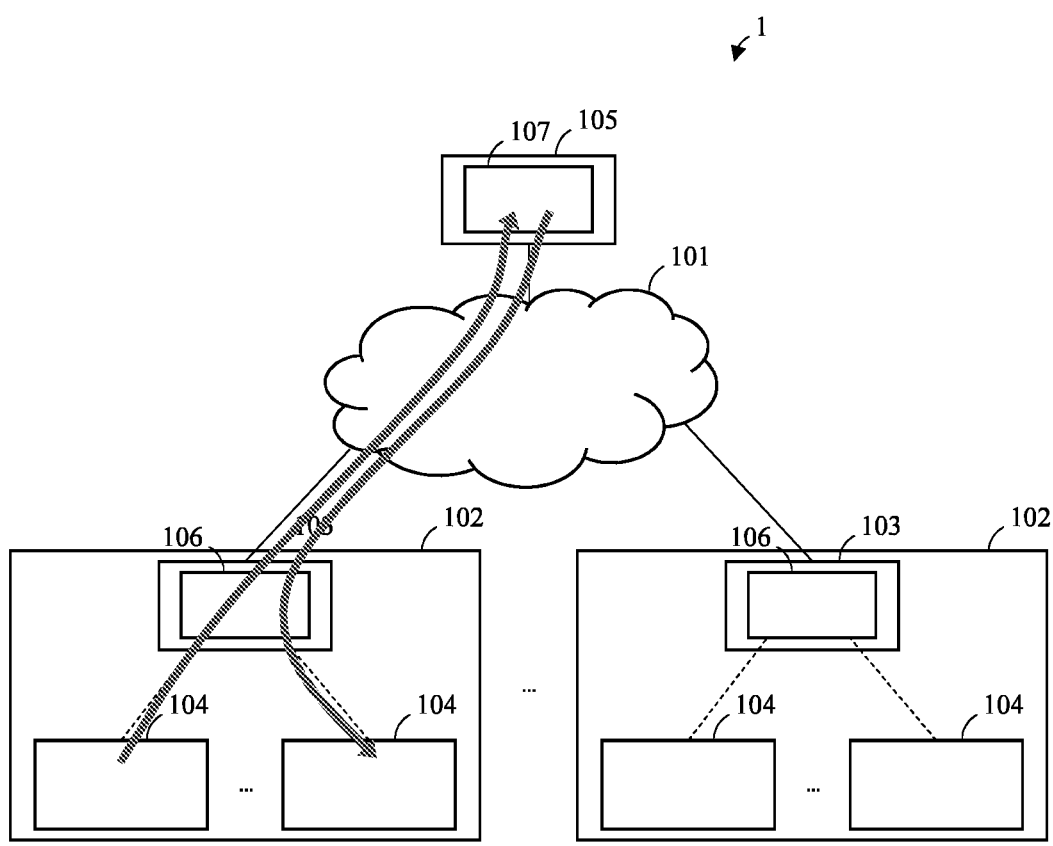
FIG. 6 illustrates a data transfer between two measurement devices of a bench of the system of FIG. 1.

FIG. 6 illustrates a data transfer between two measurement devices 104 of a bench 102 of the system 1 of FIG. 1.

In the general case, the service application 107 of the master PC 105 is configured to save and/or recall data of the at least one measurement device 104 of the at least one bench 102. In particular, the data may comprise SCPI commands, device configurations and/or measurement results. The data is particularly associated with the respective device model 202 of the at least one measurement device 104, such that the data may be re-used for potentially each of the at least one measurement device 104 of a same device model 202. For example, device configuration data saved from of one measurement device 104 may be re-used to configure another measurement device 104 of the same device model 202. For example, device configuration data may also be reset, saved and/or recalled per bench or whole lab, or copied between benches. For example, measurement results may be collected/saved per bench or whole lab. For example, firmware updates may be distributed per device model 202.

In FIG. 6, a thick grey arrow indicates that the service application 107 of the master PC 105 is configured to save data of a first one of the at least one measurement device 104 of the at least one bench 102; and to recall the saved data to a second one of the at least one measurement device 104 of the (same) at least one bench 102. The illustration implies that the involved measurement devices 104 are associated with a same device model 202.

Figure 7:
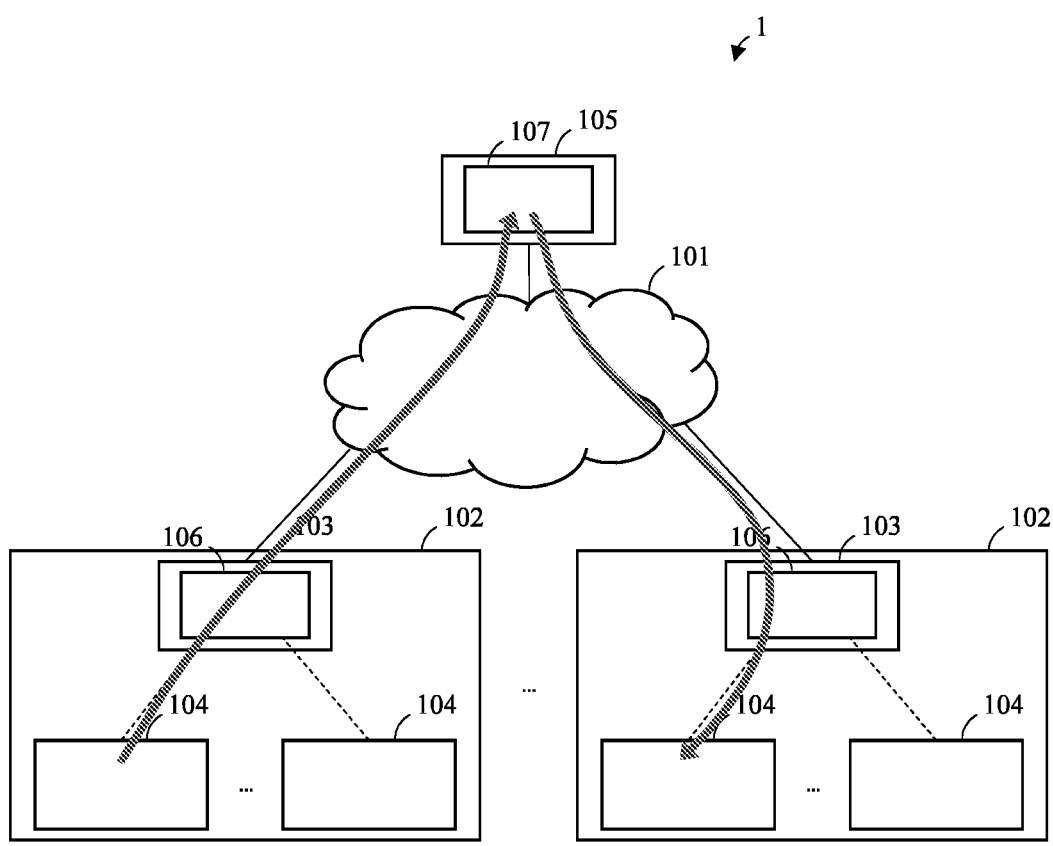
FIG. 7 illustrates a data transfer between two measurement devices of two different benches of the system of FIG. 1.

FIG. 7 illustrates a data transfer between two measurement devices 104 of two different benches 102 of the system 1 of FIG. 1.

In FIG. 7, a thick grey arrow indicates that the service application 107 of the master PC 105 is configured to save data of the at least one measurement device 104 of a first one of the two different benches 102; and to recall the saved data to the at least one measurement device 104 of a second one of the two different benches 102. This illustration implies that the involved measurement devices 104 are associated with a same device model 202 either.

The invention claimed is:

1. A system for management of lab measurement devices, comprising:
  a communication network;
  at least one bench, comprising:
    a bench PC being connected to the communication network; and
    at least one measurement device being connectable to the bench PC, and being associated with a device model; and
  a master PC external to the bench:
    being connected to the communication network, and
    being configured to manage the at least one measurement device, when connected to the bench PC, in accordance with its device model,
    wherein the bench further comprises a plurality of the measurement devices forming a self-contained arrangement to independently perform at least one specific measurement purpose,
    wherein the master PC comprises a service application being configured to
      discover the service application of the bench PC of the at least one bench and,
      receive the device model of the discovered at least one measurement device of the discovered bench PC, and
    wherein the service application of the master PC comprises a viewer being configured to
      graphically present the discovered at least one bench and the at least one measurement device of at least one bench, if any, using its device model, and
      provide a Virtual Network Computing (VNC) and/or Remote Desktop Connection (RDC) link to the service application of the bench PC of the at least one bench.

2. The system of claim 1, the bench PC comprising a service application being configured to
  discover the at least one measurement device as it is connected to the bench PC, or as it is activated when connected to the bench PC; and
  report the device model of the discovered at least one measurement device to the master PC.

3. The system of claim 2, the at least one measurement device being connected to the bench PC via an Ethernet connection.

4. The system of claim 3, the service application of the bench PC comprising a viewer being configured to provide a web link to the at least one measurement device being connected to the bench PC via the Ethernet connection.

5. The system of claim 3, the service application of the bench PC comprising a Dynamic Host Configuration Protocol (DHCP) server being configured to dynamically assign a network configuration parameter to the at least one measurement device as it is discovered by the bench PC via the Ethernet connection.

6. The system of claim 3, the service application of the bench PC being configured to arrange for port forwarding to provide remote access to the at least one measurement device being connected to the bench PC via the Ethernet connection.

7. The system of claim 6, the service application of the master PC being configured to
  discover the at least one measurement device of the at least one bench; and
  determine the device model of the discovered at least one measurement device.

8. The system of claim 2, the at least one measurement device being connected to the bench PC via a USB Test & Measurement Class (USB TMC) connection.

9. The system of claim 8, the service application of the bench PC being configured to discover the at least one measurement device via the USB TMC connection based on USB connection event subscription.

10. The system of claim 8, the service application of the bench PC comprising a remote server being configured to provide proxy access to the at least one measurement device being connected to the bench PC via the USB TMC connection.

11. The system of claim 10, the service application of the bench PC being configured to register the remote server as a program with an Open Network Computing Remote Procedure Call (ONC RPC) port mapper.

12. The system of claim 10, the remote server of the bench PC being configured to return, in response to a "*IDN?" Standard Commands for Programmable Instruments (SCPI) command, a name of the at least one bench.

13. The system of claim 10, the remote server of the bench PC being configured to return, in response to an "*OPT?" Standard Commands for Programmable Instruments (SCPI) command, a pair of:
  the device model of the at least one measurement device, and
  a port for access to the at least one measurement device.

14. The system of claim 1, the service application of the master PC being configured to search for the at least one measurement device of the at least one bench given its device model.

15. The system of claim 1 the service application of the master PC being configured to
- save and/or recall data of the at least one measurement device of the at least one bench,
- the data being associated with the device model of the at least one measurement device.

16. The system of claim 15, the data comprising Standard Commands for Programmable Instruments (SCPI) commands, device configurations and/or measurement results.

17. The system of claim 15, the service application of the master PC being configured to save data of a first one of the at least one measurement device of the at least one bench; and
- recall the saved data to a second one of the at least one measurement device of the at least one bench;
- the involved measurement devices being associated with the same device model.

18. The system of claim 15, the service application of the master PC being configured to
- save data of the at least one measurement device of a first one of the at least one bench; and
- recall the saved data to the at least one measurement device of a second one of the at least one bench;
- the involved measurement devices being associated with the same device model.

* * * * *